US011723582B2

(12) United States Patent
Johnson et al.

(10) Patent No.: US 11,723,582 B2
(45) Date of Patent: *Aug. 15, 2023

(54) NON-INVASIVE AND NON-CONTACT MEASUREMENT IN EARLY THERAPEUTIC INTERVENTION

(71) Applicant: I2DX, INC., San Francisco, CA (US)

(72) Inventors: Matthew J. Johnson, Oakland, CA (US); Janos Redei, San Francisco, CA (US); Ethan C. Green, Oakland, CA (US)

(73) Assignee: i2Dx, Inc., San Francisco, CA (US)

( * ) Notice: Subject to any disclaimer, the term of this patent is extended or adjusted under 35 U.S.C. 154(b) by 128 days.

This patent is subject to a terminal disclaimer.

(21) Appl. No.: 17/364,664

(22) Filed: Jun. 30, 2021

(65) Prior Publication Data

US 2021/0321933 A1 Oct. 21, 2021

Related U.S. Application Data

(63) Continuation of application No. 15/766,805, filed as application No. PCT/US2016/056476 on Oct. 11, 2016, now Pat. No. 11,076,798.

(Continued)

(51) Int. Cl.
*A61B 5/00* (2006.01)
*G06F 16/951* (2019.01)
(Continued)

(52) U.S. Cl.
CPC .......... *A61B 5/4082* (2013.01); *A61B 5/0022* (2013.01); *A61B 5/0077* (2013.01);
(Continued)

(58) Field of Classification Search
CPC ....... A61B 5/11; A61B 5/1101; A61B 5/1114; A61B 5/4076–4094
See application file for complete search history.

(56) References Cited

U.S. PATENT DOCUMENTS 4,306,291 A 12/1981 Zilm et al.
5,293,879 A 3/1994 Vonk et al.
(Continued)

FOREIGN PATENT DOCUMENTS

EP 1713015 A1 * 10/2006 ........... A61B 5/6868

OTHER PUBLICATIONS

Timmer, J., et al., "Quantitative analysis of tremor time series," Electroencephalography and clinical Neurophysiology, vol. 101, pp. 461-468 (1996).

(Continued)

*Primary Examiner* — Kaylee R Wilson
*Assistant Examiner* — Raymond P Dulman
(74) *Attorney, Agent, or Firm* — Maschoff Brennan

(57) ABSTRACT

Systems and methods for non-invasive and/or non-contact measurement of a subject's tremor in the context of therapeutic intervention is presented. The system includes a memory, a communications interface, a sensor to measure a signal associated with position or motion of an extremity of the subject, and a processor. The processor is configured to receive the signal from the sensor. The processor is further configured to communicate, via the communications interface, the signal, login credentials, and position or motion data to a remote server coupled to a remote electronic health record database. The remote server is configured to receive the signal from the sensor. The processor is configured to receive an analysis that quantified the severity of tremor.

18 Claims, 15 Drawing Sheets

Related U.S. Application Data

(60) Provisional application No. 62/239,604, filed on Oct. 9, 2015.

(51) Int. Cl.
*A61B 5/11* (2006.01)
*G16H 40/67* (2018.01)
*A61B 5/1172* (2016.01)
*A61B 5/01* (2006.01)
*G16H 10/60* (2018.01)
*A61B 6/03* (2006.01)
*H04L 9/40* (2022.01)

(52) U.S. Cl.
CPC .............. *A61B 5/01* (2013.01); *A61B 5/1101* (2013.01); *A61B 5/1112* (2013.01); *A61B 5/1114* (2013.01); *A61B 5/1172* (2013.01); *A61B 5/4011* (2013.01); *A61B 5/4833* (2013.01); *A61B 5/4848* (2013.01); *A61B 6/037* (2013.01); *G06F 16/951* (2019.01); *G16H 10/60* (2018.01); *G16H 40/67* (2018.01); *H04L 63/0876* (2013.01); *A61B 5/7257* (2013.01); *A61B 2560/0233* (2013.01); *A61B 2562/0204* (2013.01); *A61B 2562/0219* (2013.01); *A61B 2562/0257* (2013.01)

(56) References Cited

U.S. PATENT DOCUMENTS

| | | | |
|---|---|---|---|
| 6,601,010 | B1 | 7/2003 | Fowler et al. |
| 6,648,820 | B1 | 11/2003 | Sarel |
| 8,075,499 | B2 | 12/2011 | Nathan et al. |
| 8,679,038 | B1 | 3/2014 | Giuffrida |
| 8,920,345 | B2 | 12/2014 | Greenberg et al. |
| 9,107,614 | B2 | 8/2015 | Halkias et al. |
| 9,125,605 | B2 | 9/2015 | Tone et al. |
| 11,076,798 | B2 | 8/2021 | Johnson et al. |
| 2003/0023191 | A1 | 1/2003 | Tripp |
| 2008/0242949 | A1 | 10/2008 | Jung et al. |
| 2008/0243005 | A1 | 10/2008 | Jung et al. |
| 2009/0005654 | A1 | 1/2009 | Jung et al. |
| 2010/0030119 | A1 | 2/2010 | McNames et al. |
| 2011/0102568 | A1 | 5/2011 | Bonnet et al. |
| 2013/0041290 | A1 | 2/2013 | Kording |
| 2013/0338539 | A1 | 12/2013 | Bailey et al. |
| 2014/0074180 | A1 | 3/2014 | Heldman et al. |
| 2014/0194720 | A1* | 7/2014 | Hua .................. A61B 5/1123 |
| 2014/0257047 | A1 | 9/2014 | Sillay |
| 2015/0164377 | A1 | 6/2015 | Nathan et al. |
| 2016/0015994 | A1* | 1/2016 | Cabrerizo ............ A61B 5/4064 607/45 |
| 2016/0081609 | A1 | 3/2016 | Stanford et al. |
| 2016/0198998 | A1 | 7/2016 | Rahimi et al. |
| 2016/0262685 | A1 | 9/2016 | Wagner et al. |

OTHER PUBLICATIONS

Johnson, M..J., "Detection of Parkinson Disease Rest Tremor," Washington University in St. Louis, Engineering and Applied Science Theses & Dissertations, pp. 1-154, accessible at https://openscholarship.wustl.edu/eng_etds/12, published Oct. 10, 2014.

Postuma, R.B., et al., "Risk Factors for Neurodegeneration in Idiopathic Rapid Eye Movement Sleep Behavior Disorder: A Multicenter Study," Annals of Neurology, vol. 77, pp. 830-839 (May 2015).

Schrag, A., et al., "Prediagnostic presentations of Parkinson's disease in primary care: a case-control study," Lancet Neurol, vol. 14, pp. 57-64 (Nov. 27, 2014).

Berendse et al. Diagnosing premotor Parkinson's disease using a two-step approach combining olfactory testing and DAT SPECT imaging, 2009, Elsevier, Parkonism and Related Disorders 1583, S26-S30 (2009).

Xbox 360 Slim 4GB with Kinect, Sep. 24, 2014, Amazon.

International Search Report and Written Opinion in PCT/US2016/056476 dated Jan. 9, 2017.

* cited by examiner

| Mean (m$^{-4}$) | Standard Deviation (m$^{-4}$) | P-Value | T-Value |
|---|---|---|---|
| X- Axis | $-1.31424 \times 10^{-9}$ | 0.0028155 | 0.995 | 0.00066093 |
| Y- Axis | $2.43943 \times 10^{-6}$ | 0.00805032 | 0.9888 | 0.014 |
| Z- Axis | $-1.02269 \times 10^{-8}$ | 0.00461492 | 0.9919 | 0.0102 |
| Magnitude | $8.18441 \times 10^{-8}$ | 0.00219943 | 0.9858 | 0.0178 |
FIG. 7

```
*Client side pseudocode*
1. while TestOngoing {
2.      if handIsInVolumeArea {
3.          if handVelocity < handVelocityThreshold for 1 second {
4.              if CurrentTestTime < TestDuration {
5.                  if currentDataConfidence >   confidenceThreshold
                    AND handIsInVolumeArea
                    AND handVelocity < handVelocityThreshold {
6.                      appendNewDataPoints()
7.                  } else {
8.                      deleteRecordedData()
9.                      repeat from step (1)
10.                 }
11.             } else { //Test time has elapsed
12.                 sendDataToAnalysis()
13.             }
14.         }
15.     }
16. }
```

Figure 13

*Analyze Test Data Pipeline*

*Euclidean Distance*
   1. if evenlySpacedData{
   2.     splineFitData()
   3.     resampleSpline()
     }
   4. translateCoordinates()
   5. getEuclideanDistance()
   6. getDisplacementOfEuclideanDistances()
   7. eliminateDataSkips()
   8. filterEuclideanDistances ()
   9. calculateEuclideanDistanceFrequencyDomain()
   10. smoothPowerSpectrum()
   11. calculateTremorStatistics()

*Displacement for Each Axis*
   1. if evenlySpacedData{
   2.     splineFitData()
   3.     resampleSpline()
     }
   4. translateCoordinates()
   5. getAxisDisplacement()
   6. eliminateDataSkips()
   7. filterDisplacements()
   6. calculateDisplacementFrequencyDomain()
   8. smoothPowerSpectrum()
   9. calculateTremorStatistics()

Figure 14

NON-INVASIVE AND NON-CONTACT MEASUREMENT IN EARLY THERAPEUTIC INTERVENTION

RELATED APPLICATION

This application is a continuation of U.S. application Ser. No. 15/766,805, filed on Apr. 6, 2018, which is a 371 National Stage Entry of PCT/US2016/056476, filed on Oct. 11, 2016, which claims the benefit under 35 U.S.C. § 119(e) of U.S. Provisional Application No. 62/239,604, filed Oct. 9, 2015.

TECHNICAL FIELD

The present disclosure relates to non-invasive and/or non-contact measurement of a subject's tremor in the context of therapeutic intervention. The present disclosure more particularly relates to a) identifying promising clinical drug candidates in pharmaceutical development by confirming therapeutic target engagement in-vivo, b) screening for and diagnosis of early disease such as prodromal Parkinson's Disease (PD), and c) in-office as well as home and portable monitoring of therapeutic interventions.

BACKGROUND

Tremors are typically defined as abnormal and oscillatory movements of the body and are one of the first and most recognized physical symptoms of Parkinson's disease (PD). As with all progressive diseases, the symptoms of Parkinson's disease typically worsen over time and tremor is no exception.

In a recently published paper in Lancet Neurology (Schrag et al, 2014), the most common prediagnostic symptom of Parkinson's disease within 2 years before diagnosis (n=7232) was tremor, with 41% of individuals reporting symptoms to their General Practitioner (GP) compared with less than 1% of controls (n=40541). Further, Postuma et al (2015) reported tremor as a prodromal symptom with a 2.3× odds ratio for conversion in RBD subjects vs RBD non-converters.

The current clinical standard for measuring tremor in Parkinson's disease is the Unified Parkinson Disease Rating Scale (UPDRS) scoring, where a clinician performs a qualitative assessment resulting in a score.

BRIEF DESCRIPTION OF DRAWINGS

FIG. 7 illustrates calculated statistics of sample data for the calculated displacement of the magnitude of the X, Y, and Z axes;

FIG. 13 illustrates an embodiment of the pseudocode pipeline;

FIG. 14 illustrates an embodiment of the pseudocode pipeline for the data analysis, performed either in the client software or data analytics server.

DETAILED DESCRIPTION

Figure 1:
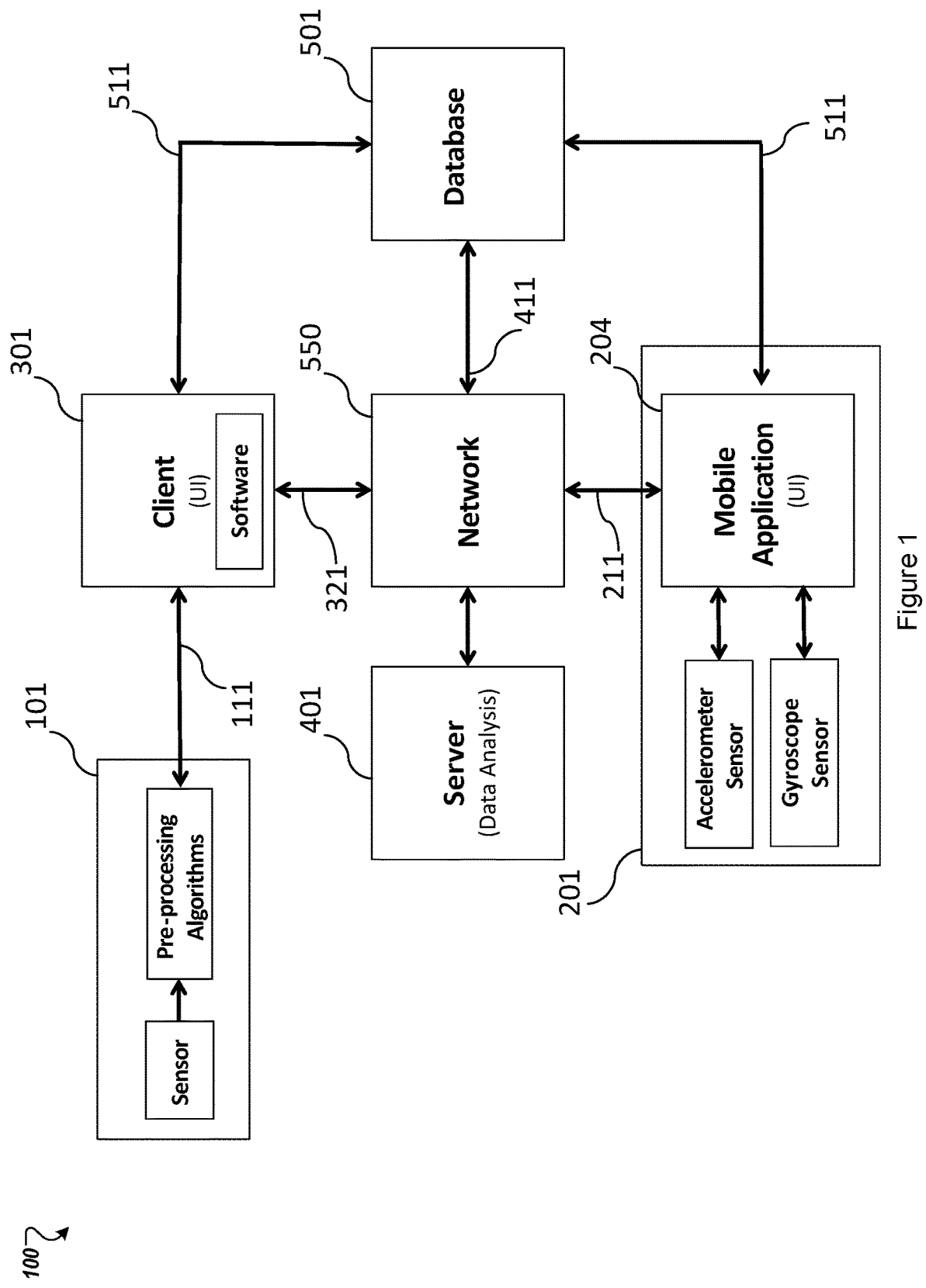
FIG. 1 illustrates a block diagram of an example operating environment of a diagnostic and/or therapeutic intervention system that measures and analyzes the severity of limb tremor.

Although some quantitative methods for measuring and analyzing tremor currently exist, they are limited. Many of these methods require the exact placement of sensors on the human body, which may result in human error and may distort results. Laser displacement and velocity systems are sometimes accurate, but may be too delicate and may require extensive setup for practical clinical or research use. Surface electromyography (EMG) is not sensitive enough to provide useful measurements of low-amplitude tremor, and the additional weight of accelerometers attached to the body can produce distorted results.

Conventional commercially available systems may not allow noninvasive and/or non-contact tremor measurement, and suitable for use in the context of early disease therapeutic intervention such as during drug development, and beyond in clinical application thereafter. Currently, many of the commercially available systems may require some type of physical contact to be made with a sensor, such as being affixed to the body part to be measured. Most direct approaches of assessing drug target engagement in humans during drug development, such as molecular assays or molecular imaging probes, may either require an invasive step such as blood sampling, or use of radiation and/or imaging agents.

Aspects of the present disclosure may relate to accurately and objectively quantify the severity of tremor using a non-contact measurement for use in the context of early therapeutic intervention, particularly with disease-modifying drug therapy in PD. Non-drug early intervention approaches such as brain stimulation (with DBS, TMS, tDCS, TENS, etc.), focused ultrasound, and the like could also be used. The present disclosure further allows for the analysis and storage of the severity of tremor at a separate remote location such as from a client computer with low processing power and in a clinical drug trial or for telemedicine use case. The disclosure further provides in-office as well as home and mobile monitoring of the results of the analysis. In addition, the disclosure allows physicians or clinicians remote access to the results of the analysis.

In one embodiment, the present disclosure includes a limb tracking system that includes a sensor that is capable of measuring signals corresponding with a subject's limb positions over time without requiring the subject to wear or attach any external sensors to the body. The signal is then transmitted either via wired or wireless connection to the client software, located on a personal computer. The client software then calculates the severity of the subject's hand tremor based on the three-dimensional position or motion signals from the sensor. The calculated severity is then compared to at least one reference value, coding the severity of tremor, such as with a given color.

In another embodiment, the present disclosure includes a hand tracking system that measures and transmits the position signals to a computer. The signals are electronically transferred to a data analytics unit, where the severity of the subject's hand tremor and tremor characteristics are calculated based on the three-dimensional position signals. The calculated severity is then compared to at least one reference value, coding the severity of tremor with a given color. The results of the tremor severity calculated in the data analytics unit are then electronically transmitted to an Electronic Health Record (EHR) Database for storage and future retrieval. Upon storage, the client software then receives the results to display to the subject on their computer.

In yet another embodiment, the present disclosure includes a hand tracking system that measures and transmits position signals to a computer where it is electronically transferred to a data analytics unit to calculate the tremor severity, which then transmits the results to an Electronic Health Record (EHR) Database for storage. Upon storage, the mobile application receives and displays the results to the subject on a smart phone or smart watch.

Another embodiment of the present disclosure includes a smart watch/smart phone system, which includes at least one sensor that is capable of measuring signals corresponding with the movement of the device, such as acceleration or gyroscopic data. This signal is then received by a mobile application on the subject's smart phone and transmitted to a data analytics unit, where the severity of the subject's hand tremor as well as tremor characteristics are calculated based on the acceleration and gyroscope signals. The results of the tremor severity calculated in the data analytics unit are then electronically transmitted to an Electronic Health Record (EHR) Database for storage, based on login credentials. Upon storage, the mobile application queries for and displays the results to the subject on the smart phone/smart watch system.

A system to analyze a subject's tremor includes a memory, a communications interface, a sensor to measure a signal associated with position or motion of an extremity of the subject, and a processor operatively coupled to the memory, the communications interface, and the sensor. The processor is configured to receive the signal from the sensor. The processor is further configured to communicate, via the communications interface, the signal, login credentials and position or motion data to a remote server coupled to a remote electronic health record database. The remote server is configured to receive the signal and perform an analysis that quantifies a severity of tremor based on the position or motion signals of the subject. The processor is configured to receive the analysis that quantified the severity of tremor and cause the quantified severity of tremor to be displayed via a display device.

The previous and following depictions are examples of the present disclosure and are intended to provide a framework to understand the components, methods, and characteristics of the embodiments disclosed herein. The included drawings are provided to allow for a more detailed understanding of the present disclosure as well as to illustrate various embodiments. The written descriptions together with the drawings and illustrations serve to further expand on the details of the disclosure.

The following detailed description references the accompanying drawings. The same reference numbers identify the same elements and components throughout the different drawings. The following description does not encompass the entire framework and scope of the present disclosure and is therefore used to serve as a mere embodiment of the disclosure and does not limit the scope of the appended claims.

The present disclosure may include non-invasive and non-contact measurement of a subject's tremor in the context of early therapeutic intervention. The devices, systems, and methods involved in the various embodiments described are used to measure, analyze, quantify, score, display and monitor human tremors. These tremors include, but are not limited to, those tremors experienced in various movement disorders such as Parkinson's disease (PD) that may occur at rest, posture, or during an action.

FIG. 1 illustrates a block diagram of an example operating environment 100 of a therapeutic intervention system, arranged in accordance with at least one embodiment described herein. The operating environment 100 includes at least one client device 101, 201, 301, a server 401, at least one database 501, and a network 550. The client devices 101, 201, 301, the server 401, the database 501, (collectively, "environment components") may be communicatively coupled via the network 550. The environment components may communicate data and information, such as messages pertaining to questions, solutions and/or services communicated from the server 401 to the client devices 101, 201, 301 via the network 550. Each of the environment components is briefly described in the following paragraphs.

The client devices 101, 201, 301 may include a processor-based computing system. The client devices 101, 201, 301 each may include memory, a processor, and network communication capabilities. In the operating environment 100, the client devices 101, 201, 301 may be capable of communicating and receiving data and information to and from the server 401 via the network 550. Some examples of the client devices 101, 201, 301 may include a mobile phone, a smartphone, a tablet computer, a laptop computer, a desktop computer, a set-top box, a wearable device, a watch, a smart watch, a virtual-reality device, or a connected device, etc. The client devices 101, 201, 301 may include one or more sensors to detect information pertaining to a user of the client devices 101, 201, 301, an environment in which the client devices 101, 201, 301 is situated, etc. The one or more sensors may include at least one of a clock, camera, microphone, gyroscope, accelerometer, infrared sensor, global positioning system (GPS), near-field communication (NFC) sensor, brightness sensor, proximity sensor, compass, thermometer, step counter, or fingerprint sensor, etc.

The server 401 may include a processor-based computing device. For example, the server 401 may include a hardware server or another processor-based computing device configured to function as a server. The server 401 may include memory and network communication capabilities. In the operating environment 100, the server 401 may be configured to communicate with the client device 301 and the database 501 via the network 550.

The database 501 may include any memory or data storage. The database 501 may include network communication capabilities such that the environment components may communicate with the database 501. In some embodiments, the database 501 may include computer-readable storage media for carrying or having computer-executable instructions or data structures stored thereon. The computer-readable storage media may include any available media that may be accessed by a general-purpose or special-purpose computer, such as a processor. For example, the database 501 may include computer-readable storage media that may be tangible or non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and that may be accessed by a general-purpose or special-purpose computer. Combinations of the above may be included in the database 501. The database 501 may include an Electronic Health Record (EHR) database 501.

The database 501 may store various data. The data may be stored in any data structure, such as a relational database structure.

The network 550 may include a wired network, a wireless network, or any combination thereof. The network 550 may include any suitable topology, configuration or configurations including a star configuration, token ring configuration, or other configurations. The network 550 may include a local area network (LAN), a wide area network (WAN) (e.g., the Internet), and/or other interconnected data paths across which multiple devices may communicate. In some embodiments, the network 550 may include a peer-to-peer network. The network 550 may also be coupled to or include portions of a telecommunications network that may enable communication of data in a variety of different communication protocols. In some embodiments, the network 550 includes BLUETOOTH® communication networks and/or cellular communication networks for sending and receiving data including via short messaging service (SMS), multimedia messaging service (MMS), hypertext transfer protocol (HTTP), direct data connection, wireless application protocol (WAP), e-mail, or the like.

As illustrated in FIG. 1, a client device (e.g., client device 101) may include one or more sensors 110 that are capable of measuring a subject's three-dimensional position or motion of one or more extremities of a subject without physical contact. These sensors 110 may be a part of, but are not limited to, a hand tracking system (e.g., client device 101). In accordance with at least one embodiment, the hand tracking system provides non-contact motion detection of a user's extremities for purposes of navigating interfaces by hand movements, instead of by a computer mouse and the like. This system includes a method for detecting, measuring, and relaying three-dimensional position data 111 of different locations on the extremities of a user. One example of such a device is marketed as "Leap Motion Controller" (Leap Motion, Inc., San Francisco, USA). Other hand tracking and motion detecting systems can also be used within the framework. For example, various depth or 3D camera and related toolkits such as Intel RealSense, Nimble Sense, Reactiv Touch+ can be utilized.

In an embodiment, the hand tracking system (e.g., client device 101) acts as a peripheral and interfaces with a personal computer (e.g., client device 301) through a wired (e.g., Universal Serial Bus (USB)) connection. In an alternate embodiment, the hand tracking system may interface with the personal computer 301 via wireless methods such as Bluetooth, Bluetooth Low Energy (BLE), or through a Wireless-Fidelity (Wi-Fi) service method. The personal computer 301 may include a laptop, tablet, or desktop computer. In yet another embodiment, the hand tracking system 101 is integrated in a client computer 301 such as a personal computer, or integrated in/attached to mobile phone, or another portable or wearable computer such as a head mounted computer, goggles or glasses. In an embodiment, said computer such as personal computer 301 runs client software 311 that may serve as the user interface to instruct or guide the user to operate the hand tracking system 101 or relay information such as raw data from the hand tracking system 101 or analysis of the data to the user. Further, the client software 311 may communicate with the hand tracking system 101 to collect and aggregate three-dimensional position data 111, and may control the hand tracking system 101.

Further, in an embodiment, the client software 311 may also perform real-time or post-processing of the three-dimensional position data 111 to determine whether the data being recorded is optimal, whether the user is performing the instructed tasks correctly, in order to minimize the amount of error and improve the accuracy of the measurements such as the pseudocode shown in FIG. 13. In an embodiment, once a test or recording has started the position of the hand or fingers are constantly checked for their three-dimensional position to ensure that the hand is in the correct position for recording or in the most optimal volume space in relation the hand tracking system 101. Within a specified amount of time at the beginning of the recording, the hand or fingers are checked to ensure that they are not purposefully moving by calculating and comparing the instantaneous velocity of the hand, which may include measuring the palm, against a predetermined velocity threshold. The purpose of this procedure is to not only ensure that the user is not moving their hand around, which could introduce error into the tremor analysis, but also to confirm that the positions reported by the hand tracking system 101 are accurate and not unreasonable. The length of time of the recording is also continually checked to ensure that it does not exceed the pre-set time of the recording. If the length of time of the data recorded has not exceeded the pre-set time threshold, a metric either provided by the hand tracking system 101 or calculated by the data provided by the hand tracking system 101 is used to determine the confidence level of the accuracy of the hand tracking system 101. If this confidence level is below a pre-determined threshold, the recorded data is deleted and the test as well as recording is restarted. If the confidence level is above the pre-determined threshold, the recording continues. The hand position is also continually checked during the recording to ensure that the hand is still within a predetermined volume, if the hand moves out of this predetermined volume then the recording is deleted and restarted. Similarly, the velocity of the hand is constantly checked to make sure that it doesn't pass a predetermined velocity threshold to make sure the hand is held as steady as possible and to confirm that the data from the hand tracking system 101 is reasonable and not outputting unreasonable values throughout the recording. If the velocity of the hand passes the pre-set velocity threshold, the recorded data is deleted and the recording is restarted. If all the conditions for ensuring correct data from the hand tracking system 101 and for ensuring that the user is performing the test correctly are met, then the data is recorded and is appended to currently existing recording. Once the test duration reaches the predetermined test length, the data is then sent to another pipeline for data analysis.

The client software 311 may communicate with remote servers, such as a remote server/data analytics unit 401. The client software 311 may send the recorded three dimensional position data along with other information 321, such as login credentials like a user identification number and password, to the remote server/data analytics unit 401. In this embodiment, the remote server/data analysis unit 401 may calculate various tremor characteristics and features useful in quantifying tremor, where the analysis may follow pseudocode similar to FIG. 14. In this embodiment, the analysis includes checking the recorded data to determine whether the hand tracking system 101 has a consistent frame rate and the data samples are evenly spaced in time. If the hand tracking system 101 does not have a consistent sampling rate, a polynomial spline may be fit to the data set and then resampled at a constant sampling rate to estimate the position signals in the three dimensions. Once the data has a constant sampling rate and the data points are evenly spaced in time, the coordinate system used to record the positions is translated so that equal weight is given to the three axes, when displacement from origin is calculated. For example, the first data point of three dimensional position in (x, y, z) recorded may be (200 mm, 100 mm, 600 mm) in relation to the origin of the hand tracking system 101, but this point would be translated to a position such as (200 mm, 200 mm, 200 mm) and the same equations used for this translation would be appropriately applied to the rest of the data. Once translated, the position data may be used to calculate the Euclidean distance, based on the three-dimensional position, from this translated origin for each frame. The difference between the Euclidean distances may then be calculated, between frames to determine the change in distance from the translated origin, to determine the change in position over time. The translated position data may also be used to calculate the displacements between frames for each individual axis. The differences in the Euclidean distance and displacements for each axis may then be checked for data integrity, by checking for statistical anomalies. For example, one may accomplish this by checking for values that exceed the mean of the values with the addition of a certain number of standard deviations or removing values that are below the mean with the subtraction of a certain number of standard deviations. This data may then be filtered using a band-pass filter to isolate the frequencies of interest and then converted to the frequency domain using a Fast-Fourier transform or other method, or may be performed in the reverse order. Once in the frequency domain the signal may be smoothed using either adaptive or non-adaptive smoothing techniques. The smoothed signal may then be used to calculate various tremor characteristics such as, but not limited to peak amplitude, peak frequency, frequency dispersion, and proportional power within various frequency bands.

In addition to the hand tracking system 101, the embodiment may, but not necessarily, include a smart watch/smart phone system (e.g., client device 201). The smart watch/smart phone system 201 may include a smart phone, a smart watch, or both. A smart watch may refer to a wearable technology worn on the wrist, hand, leg, or finger (or any other body part) that contains one or more computing units with a CPU and memory and one or more communication units such as but not limited to Wi-Fi, Bluetooth, or cellular modem units (3G, 4G, LTE) capable of relaying information wirelessly. This smart watch/smart phone system 201 may include sensors for measuring motion such as but not limited to accelerometers and gyroscopes. Further, the smart watch/smart phone system 201 may contain mobile software or a mobile application 204 to provide a user interface that allows the user to enter log in credentials, view current and past information graphically or numerically, and provides access to data from onboard sensors, should they exist. In an embodiment, information 211 is sent from the smart watch/smart phone system 201, which may include login credentials as well as motion data from onboard sensors, to a remote server/data analysis unit 401 for data analysis. In yet another embodiment, data collected from the smart watch and/or smart watch/phone system 201 may be combined and analyzed together in the data analysis unit 401.

In an embodiment, the results of the data analysis as well as any other information 411, such as login credentials, may then be electronically sent from the remote server/data analytics unit 401 to the database 501. The information 411 sent may contain log in credentials that can be used to determine permissions within the database 501 and to determine where in the database 501 the information 411 should be saved.

An embodiment also includes communication between the client software 311 and the database 501. The client software 311 or mobile software 204 may query the database 501 using the proper credentials to gain access to results and information stored associated with the user's credentials. This information 511 may then be electronically sent from the database 501 to the client software 311 or mobile software 204.

In yet another embodiment, where the database 501 includes an EHR database, the database 501 may contain information relevant to early therapeutic intervention. The database 501 may further contain or connect to systems and data sources used in clinical research such as pharmaceutical development. Tremor data collected from the hand tracking system 101 may be stored in the database 501 and/or said clinical research system or data source, alongside clinical profiling data such as drug, dose, and patient characteristics. Tremor data may then be analyzed to determine a signal of therapeutic effect such as therapeutic target engagement in-vivo. Tremor data may further be combined with other markers such as genetic information, in-vivo imaging, lab tests, to determine such signals or profiles of efficacy. In yet another embodiment, such combined data is tremor data collected from the hand tracking system 101 and then combined with data from a smart watch and/or smart watch/phone system 201. Said signals or profiles may then be used to identify promising clinical drug candidates and stored in yet another database, analyzed by drug or between drugs to discover similarities. Machine learning, artificial intelligence (AI) or statistical approaches may further be utilized to combine said markers or discover said similarities. In yet another embodiment, said tremor data is used alone or in combination with other markers to screen for and diagnosis of early disease such as prodromal Parkinson's Disease (PD), or for enrichment in a clinical drug or therapeutic device (such as DBS) trial by selecting those patients that are most likely to respond, or identifying which patients are most likely to develop dementia, in addition to developing motor symptoms. For example, an olfactory (sniff) test and/or genetic data could be combined with tremor assessment as disclosed to direct patients to more invasive and confirmatory tests such as DAT imaging using SPECT, or PET imaging. Moreover, the tremor data as disclosed may further be utilized in an in-office setting as well as for home and portable monitoring of therapeutic interventions. In yet another embodiment, tremor data may be compared to other markers such as in-vivo imaging data and/or genetic data to determine certain tremor characteristics that can be used in patient therapeutic monitoring.

Modifications, additions, or omissions may be made to the environment 100 without departing from the scope of the present disclosure.

Figure 2:
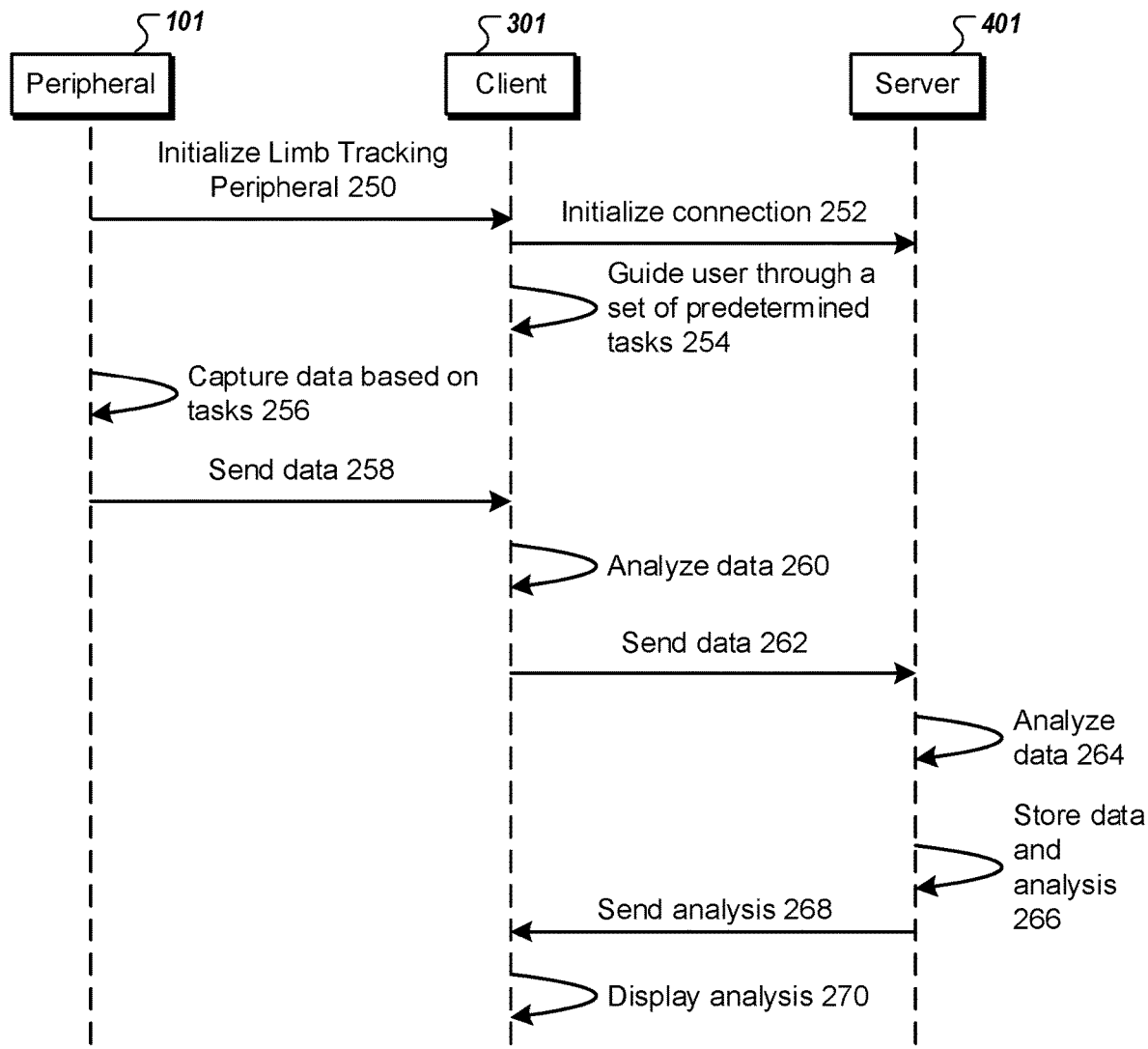
FIG. 2 illustrates a sequence diagram of an example method to measure and analyze tremor in a system that includes a peripheral measurement device connected to a client device.
Figure 3:
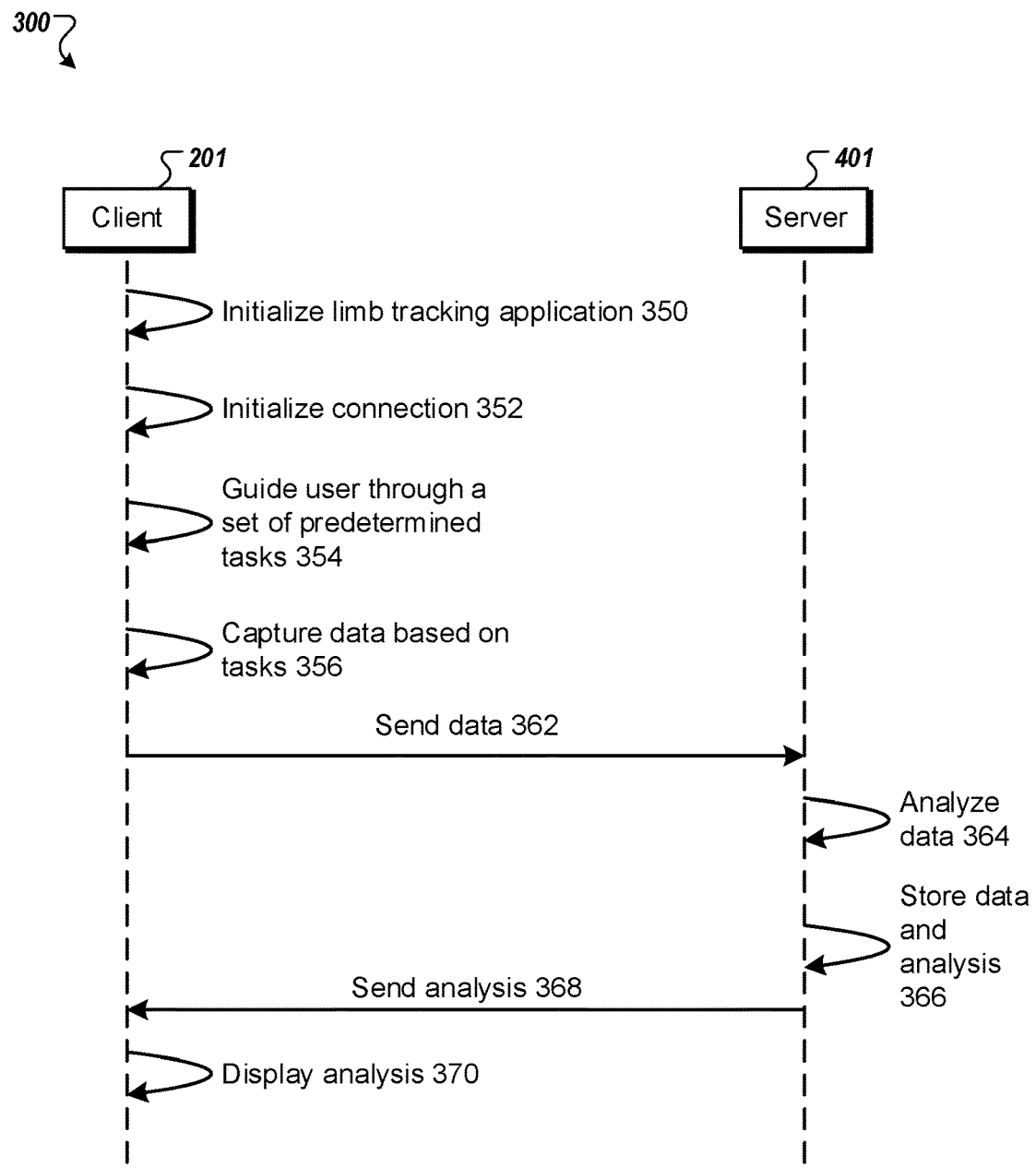
FIG. 3 illustrates a sequence diagram of an example method to measure and analyze tremor in a system that includes a client device with an integrated peripheral measurement device.

FIGS. 2-3 illustrate sequence diagrams of example methods related to a measuring and analyzing tremor in various systems. The methods may be performed by processing logic that may include hardware (circuitry, dedicated logic, etc.), software (such as is run on a general purpose computer system or a dedicated machine), or a combination of both, which processing logic may be included in the operating environment 100 of FIG. 1, or another computer system or device. However, another system, or combination of systems, may be used to perform the methods. For simplicity of explanation, methods described herein are depicted and described as a series of acts. However, acts in accordance with this disclosure may occur in various orders and/or concurrently, and with other acts not presented and described herein. Further, not all illustrated acts may be used to implement the methods in accordance with the disclosed subject matter. In addition, those skilled in the art will understand and appreciate that the methods may alternatively be represented as a series of interrelated states via a state diagram or events. Additionally, the methods disclosed in this specification are capable of being stored on an article of manufacture, such as a non-transitory computer-readable medium, to facilitate transporting and transferring such methods to computing devices. The term article of manufacture, as used herein, is intended to encompass a computer program accessible from any computer-readable device or storage media. Although illustrated as discrete blocks, various blocks may be divided into additional blocks, combined into fewer blocks, or eliminated, depending on the desired implementation.

FIG. 2 illustrates a sequence diagram of an example method 200 to measure and analyze tremor in a system that includes a peripheral measurement device 101 connected to a client device 301. The method 200 may be performed, at least in part, by a peripheral device (such as the client device 101), a client (such as the client device 301) and a server (such as the server 401).

At 250, the peripheral device 101 may be initialized with the client device 301. In at least one embodiment, a subject uses a limb tracking device 101 and initializes the limb tracking device 101 with software operating on a user's computer 301. In at least one embodiment, the client 301 receives information about the user, such as via a user interface. In at least one embodiment, user information has previously been loaded to the peripheral 101 and the client 301 may receive this user information during the initialization.

At 252, the client 301 may initialize a wired or wireless connection to a server associated with a limb tracking system. The client 301 may be configured to send at least some of the user information to the server 401. In at least one embodiment, the user information sent to the server may not personally identify the user. The server 401 may identify a set of predetermined tasks, the performance of which may help to measure and analyze tremor in the user. The server 401 may send the set of predetermined tasks to the client 301.

At 254 the client 301 may guide the user through the set of predetermined tasks. In at least one embodiment, the client 301 may prompt the user through a series of tasks, such as via a visual user interface. The tasks may include limb (e.g., hand, foot) movements or motions to be performed by the user in various directions and for various periods of time. The user may perform the series of tasks while wearing the or in range of (for non-wearable peripherals such as 3D camera) the peripheral 101 such that the peripheral 101 records the motions made by the user.

At 256 the peripheral 101 captures data based on the user's performance of the set of predetermined tasks. At 258 the peripheral 101 sends the captured data to the client 301.

At 260 the client 301 may analyze the data received from the peripheral 101. The client 301 may perform various analyses on the data. The client 301 may perform the various analyses on the data in real-time. In at least one embodiment, the client 301 may perform the various analyses on the data to ensure the validity of the data and to ensure that the user is correctly performing the tasks as directed.

At 262 the client 301 sends the data to the server 401. In at least one embodiment, the client 301 sends the data to the server after successful validation and/or a determination that the user has correctly performing all of the tasks as directed.

At 264 the server 401 may analyze the data, as described herein. In at least one embodiment, data analysis is performed by the server 401 to quantify a severity of tremor.

At 266 the server 401 may store the data and the results of the analysis. In at least one embodiment, the results of data analysis are transmitted from the server to the database, such as an EHR database for storage.

At 268 the results from the data analysis are sent to the client 301. The results may be sent directly from the server 401 or from the database such as an EHR database.

At 270 the client 301 may display the results of the data analysis to the user, such as via a graphical user interface. The results may be displayed numerically, graphically, pictorially, etc.

FIG. 3 illustrates a sequence diagram of an example method 300 to measure and analyze tremor in a system that includes a client device 201 with an integrated peripheral measurement device. The method 300 may be performed, at least in part, by a client device (such as the client device 201) and a server (such as the server 401).

At 350, an application at the client device 201 may be initialized. In at least one embodiment, the client device 201 includes a smart watch and/or a smart phone system. The client device 201 may at least partially initialize the application running on the client device 201, such as by collecting and/or requesting user information. In at least one embodiment, the client 201 receives information about the user, such as via a user interface. In at least one embodiment, user information has previously been loaded to the client 201 may receive this user information during the initialization.

At 352, the application initializes a connection to hardware of the client device 201, such as a tri-axial accelerometer or 3D camera through an available SDK.

At 354 the application guides the user through a set of predetermined tasks. The performance of the set of predetermined tasks may help the client device 201 to measure and analyze tremor in the user. The server 401 may send the set of predetermined tasks to the client 201 or the set of predetermined tasks may be preloaded onto the client device 201. In at least one embodiment, the client 201 may prompt the user through a series of tasks, such as via a visual user interface. The tasks may include limb (e.g., hand, foot) movements or motions to be performed by the user in various directions and for various periods of time. The user may perform the series of tasks while in range of a 3D camera, or by wearing the client 201, while holding the client 201, while the client 201 is in the user's pant pocket, etc., or any other mechanism to couple the client 201 to the user such that the client 201 records the motions made by the user.

At 356 the client 201 captures data based on the user's performance of the set of predetermined tasks. At 362 the client 201 sends the captured data to the server 401.

At 364 the server 401 may analyze the data, as described herein. In at least one embodiment, data analysis is performed by the server 401 to quantify a severity of tremor. The server 401 may perform the various analyses on the data substantially in real-time. In at least one embodiment, the server 401 may perform the various analyses on the data to ensure the validity of the data and to ensure that the user is correctly performing the tasks as directed.

At 366 the server 401 may store the data and the results of the analysis. In at least one embodiment, the results of data analysis are transmitted from the server 401 to the database such as an EHR database for storage.

At 368 the results from the data analysis are sent to the client 201. The results may be sent directly from the server 401 or from the EHR database.

At 370 the client 201 may display the results of the data analysis to the user, such as via a graphical user interface. The results may be displayed numerically, graphically, pictorially, etc.

Figure 4:
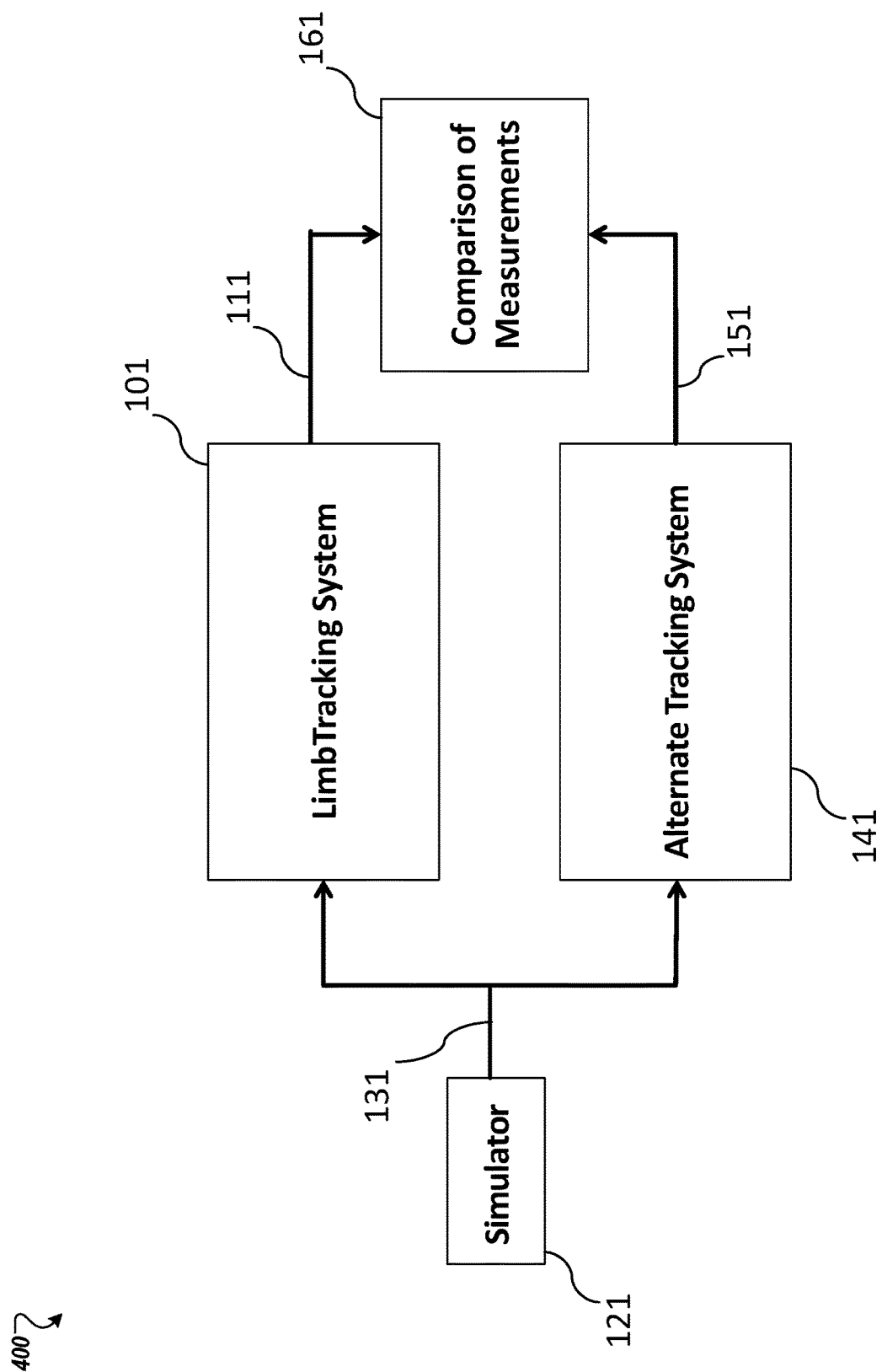
FIG. 4 illustrates a simulator system.

FIG. 4 illustrates a simulator system 400. To qualify sensors for use in drug development and subsequent clinical application, according to one embodiment, a simulator 121 may be employed. The accuracy of the hand tracking system 101 may be verified as depicted in the simplified block diagram of FIG. 4.

Figure 5:
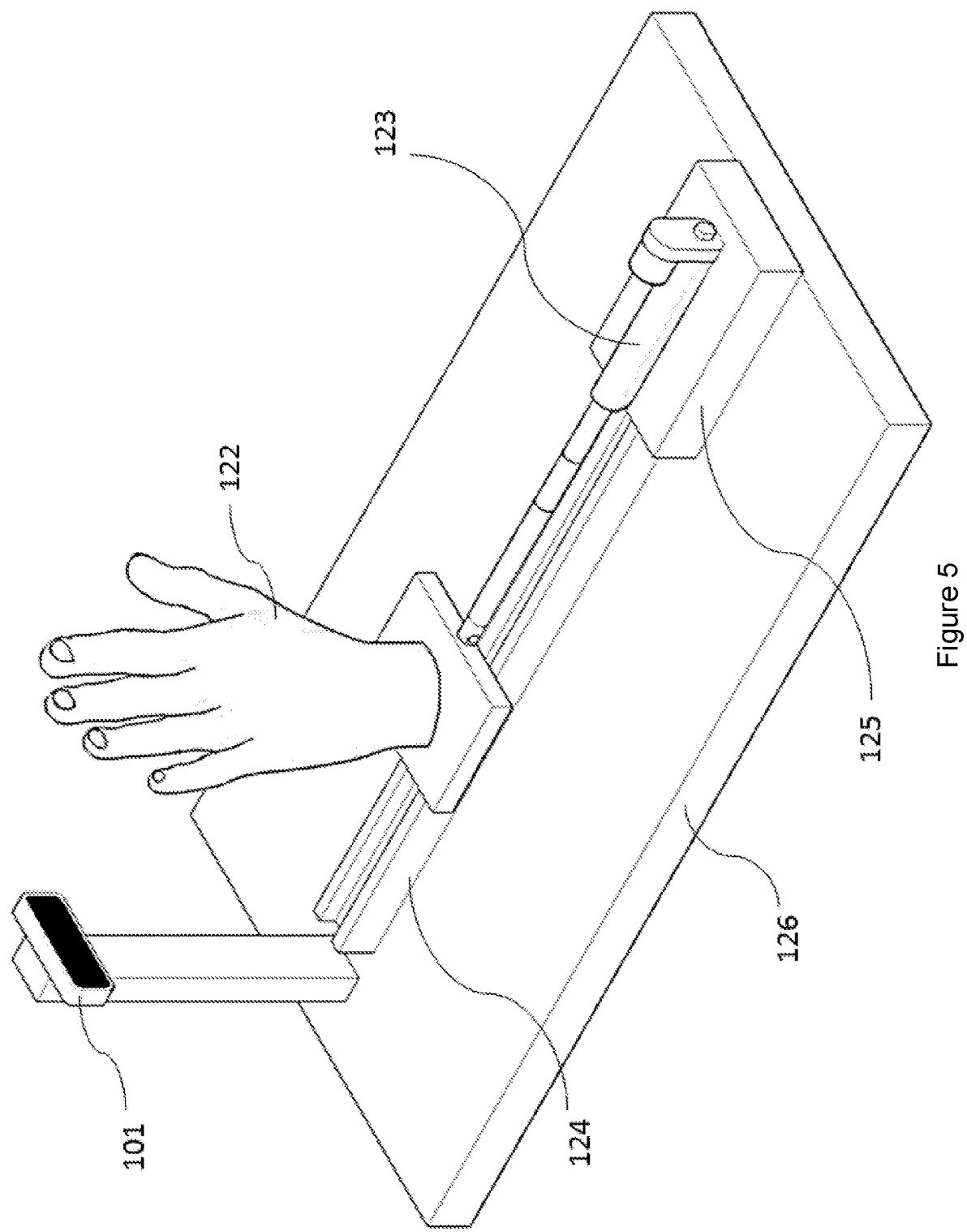
FIG. 5 illustrates an isometric view of one embodiment of a simulator.

A simulator 121, with an embodiment shown in FIG. 5, may be used to simulate human tremor. In this embodiment, a hand phantom 122 is securely mounted on a platform in front of a hand tracking system (e.g., client 101). The hand phantom 122 and platform may be secured to a sliding track 124, to limit friction and limit movement to one axis. The hand phantom 122 and platform may further be attached to a linear actuator 123, to move the hand phantom 122 in a prespecified motion. The linear actuator 123 may be controlled via a control board 125 or other method that allows for reproducible motion. One example of such a control board is marketed as "Linear Actuator Control Board" by Firgelli Technologies, Inc. (Victoria BC, Canada). In the embodiment the sliding track 124, the linear actuator 123, and the hand tracking system 101 may be secured to a mounting board 126 for example, to provide better reproducibility and portability. The simulator creates a reproducible movement 131 that may be analyzed using an alternate tracking system 141. This alternate tracking system 141 may include calculations from the linear actuator 123, control board 125, a high-resolution camera, laser measurement system, or other method independent of the hand tracking system 101. The resulting positions 151 obtained or calculated from the alternate tracking system 141 and resulting positions 111 from the hand tracking system 101 may then be compared with one another 161 to determine the accuracy and reproducibility of the hand tracking system 101 as a method of qualifying said sensors and/or hand tracking system. Similarly, the accuracy and reproducibility of a wearable sensor (e.g., client device 201 in FIG. 1) may be verified by mounting the sensor on the hand phantom 122. In yet another embodiment, the alternate tracking system is an already qualified reference hand tracking system that is then used to qualify additional hand tracking systems that will be distributed for use in clinical drug development or clinical practice.

By way of example, FIGS. 6-12 illustrate sample results for said comparison 161. One method of comparison 161 is a measurement of the real positions 131 of the simulator while the simulator is turned off and the hand phantom is at rest, where it is known that true values of the positions 131 are constant, resulting in no displacement. Therefore, the null hypothesis would be that the data follows a normal distribution with a mean displacement of zero and zero variance.

Figure 6:
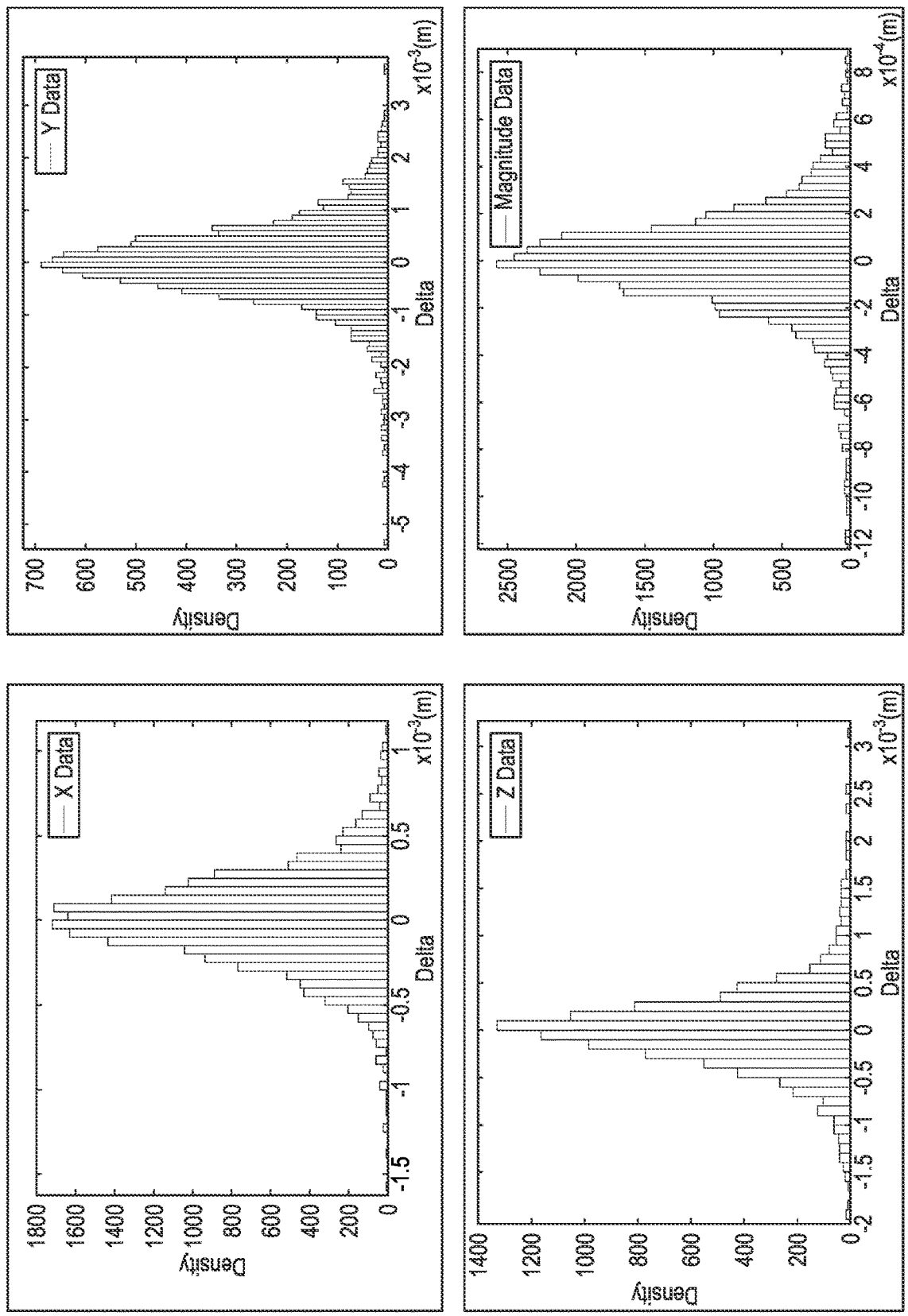
FIG. 6 illustrates sample data obtained using a simulator.

FIG. 6 illustrates sample data that may include 2297 samples that were obtained using a simulator with an embodiment similar to that of FIG. 5 and a "Leap Motion Controller" for the hand tracking system 101, where the phantom hand 122 remained stationary during the recording. The distribution of the displacement of the magnitudes of the three axes of positions passed the conditions of a normal distribution.

FIG. 7 illustrates a two-sample t-test of the dataset shown in FIG. 6 against a dataset with a zero mean and zero variance at 0.01 significance level, where the critical T-value is 2.6. As demonstrated in FIG. 7, the sample data supports the null hypothesis that the data shown in FIG. 6 is a part of a dataset that includes a zero mean and zero variance.

Another possible method of comparison 161 includes a tremor characteristic that measures and calculates the dominant frequency of a given movement, after it has been filtered.

Figure 8:
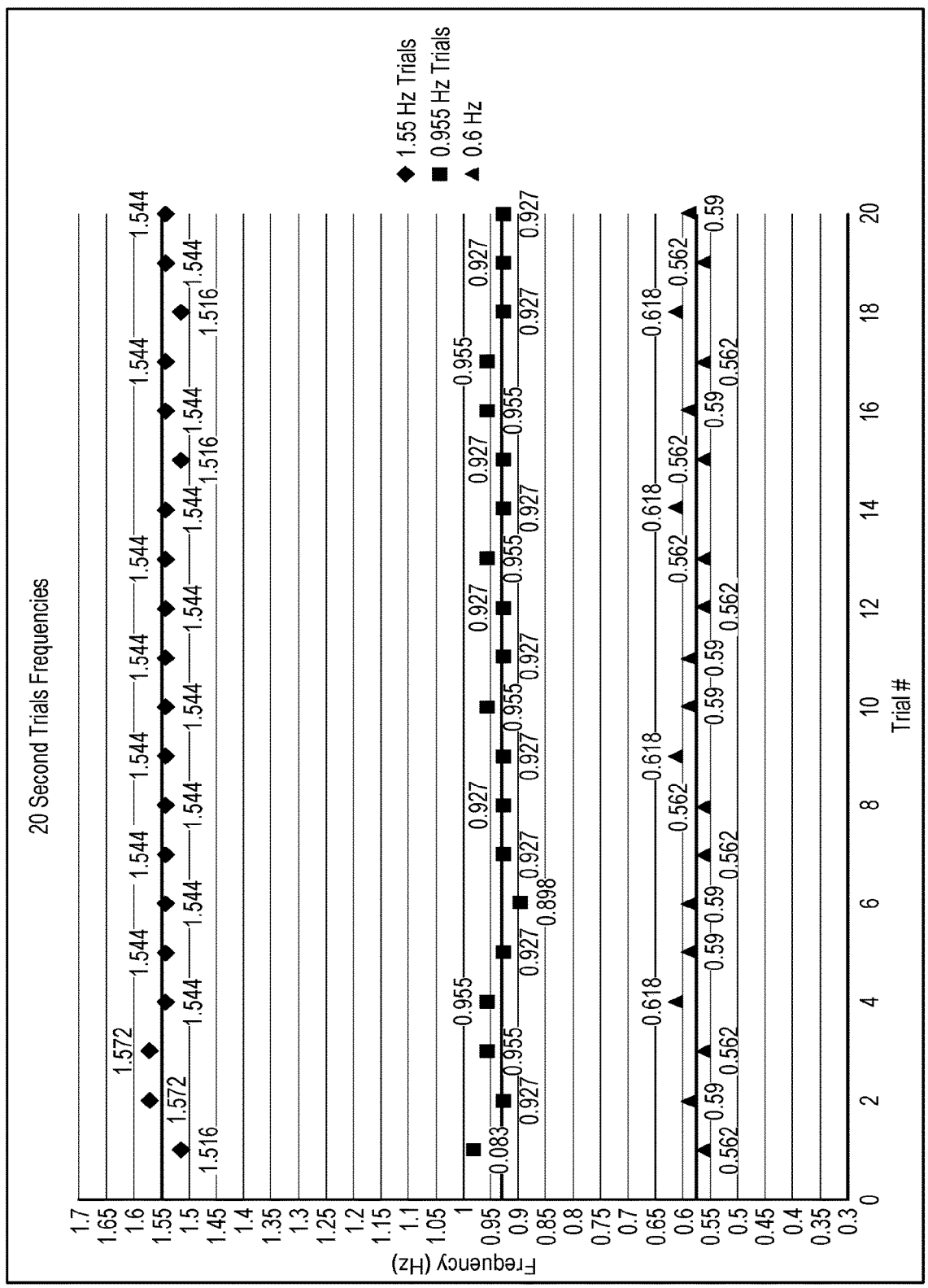
FIG. 8 illustrates sample results of calculated frequencies from 20 trials (tests) of 20 second recordings, with known frequencies using a simulator.
Figure 10:
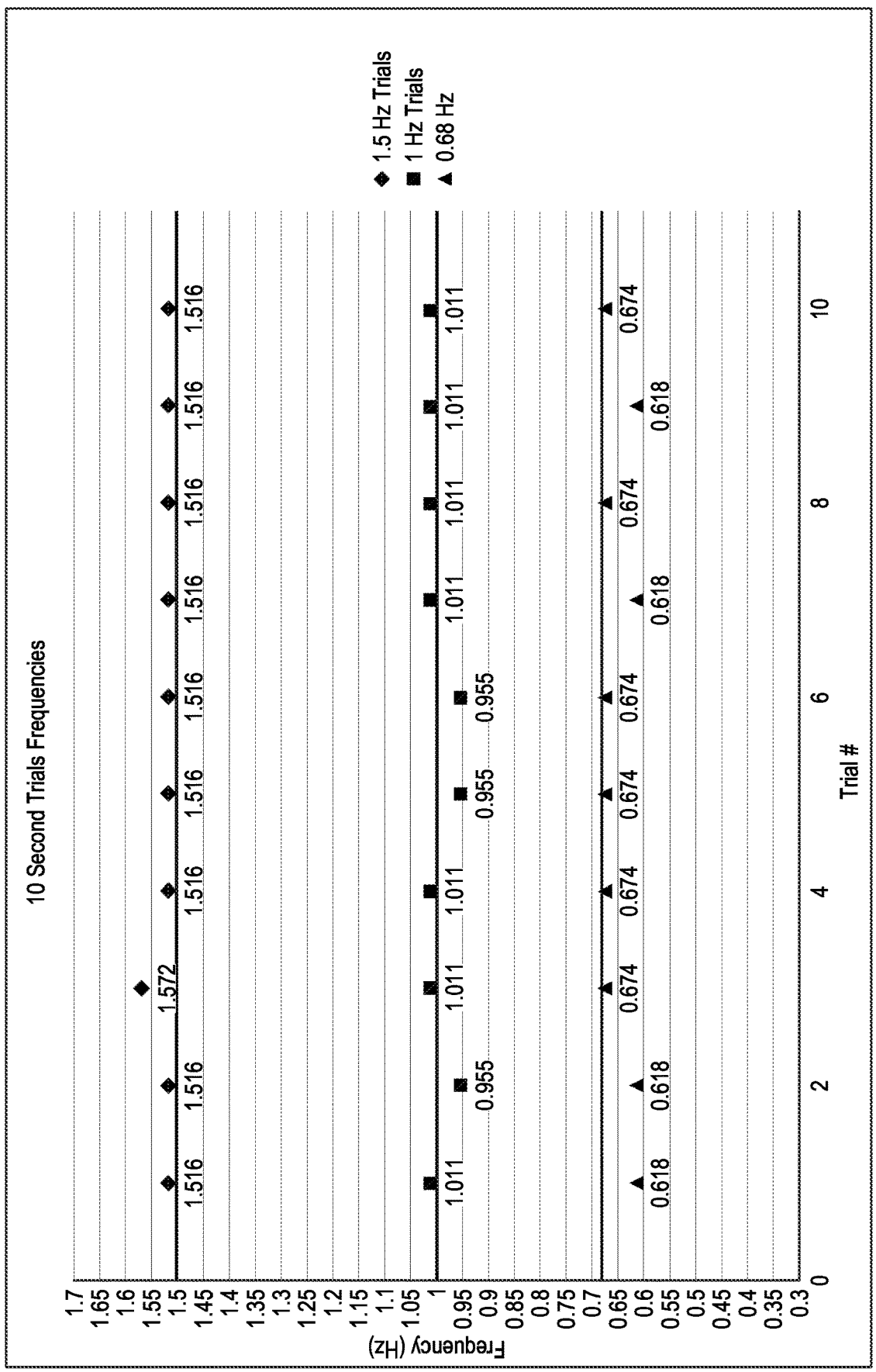
FIG. 10 illustrates sample results of calculated frequencies from 10 trials of 10 second recordings, with known frequencies using a simulator.
Figure 12:
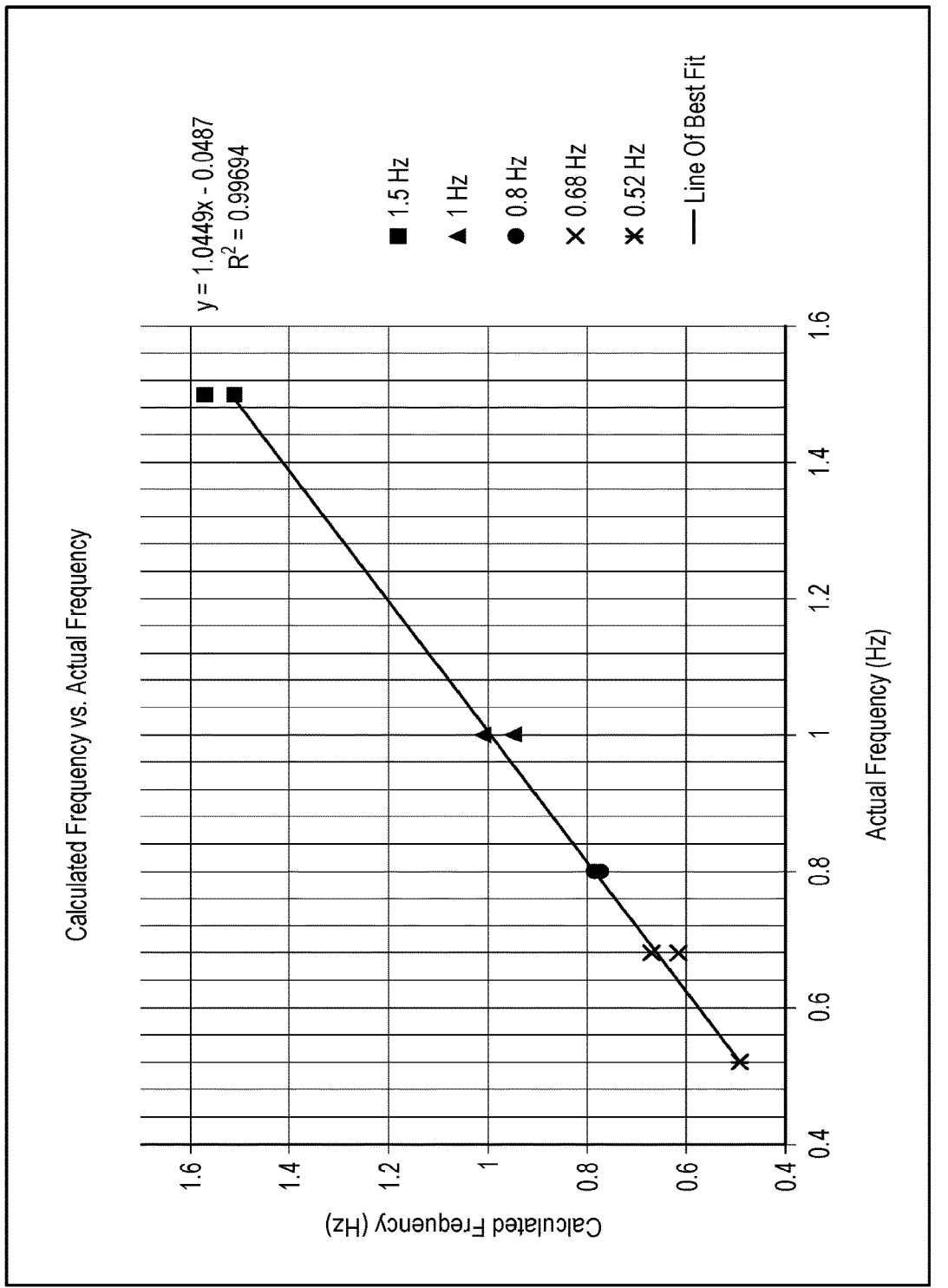
FIG. 12 illustrates a plot of sample data of actual frequency versus calculated frequency, for various different known frequencies along with a line of best fit and relevant statistics.

FIG. 8 illustrates sample results again using a "Leap Motion Controller" as the hand tracking system 101 and a simulator with an embodiment similar to that of FIG. 5. These sample results may include 20 different recordings lasting 20 seconds each at three different frequencies, where the dominant frequency was pre-determined using a control board 125 and verified using high-resolution video as the alternate tracking system 141. The calculated frequencies from the "Leap Motion Controller" were compared to the known predetermined frequencies and plotted to determine repeatability and accuracy. Similarly, FIG. 10 illustrates different sample results using the same method mentioned, but instead may include 10 different recordings lasting 10 seconds each for three different frequencies. Using these different lengths of recordings may assist in determining whether utilizing less data, from a shorter test, still provides accurate results for determining the dominant frequency. FIG. 12 illustrates a plot of the aggregation of different predetermined dominant frequencies and how they compare to the calculated dominant frequency, using the before mentioned method. A linear regression may be fit to the data, where the closer the R-squared value of the linear regression is to a value of one the more accurate the calculated dominant frequencies are to the known predetermined dominant frequencies. As demonstrated in FIG. 12, using the "Leap Motion Controller", the calculated dominant frequencies are shown to have a near perfect linear regression with an R-squared value of approximately 0.99694 suggesting that the calculated dominant frequencies are accurate.

Yet another method of comparison 161 may include a tremor characteristic that involves measuring and calculating an estimation of the amplitude of displacement of a given movement at the dominant frequency after filtering.

Figure 9:
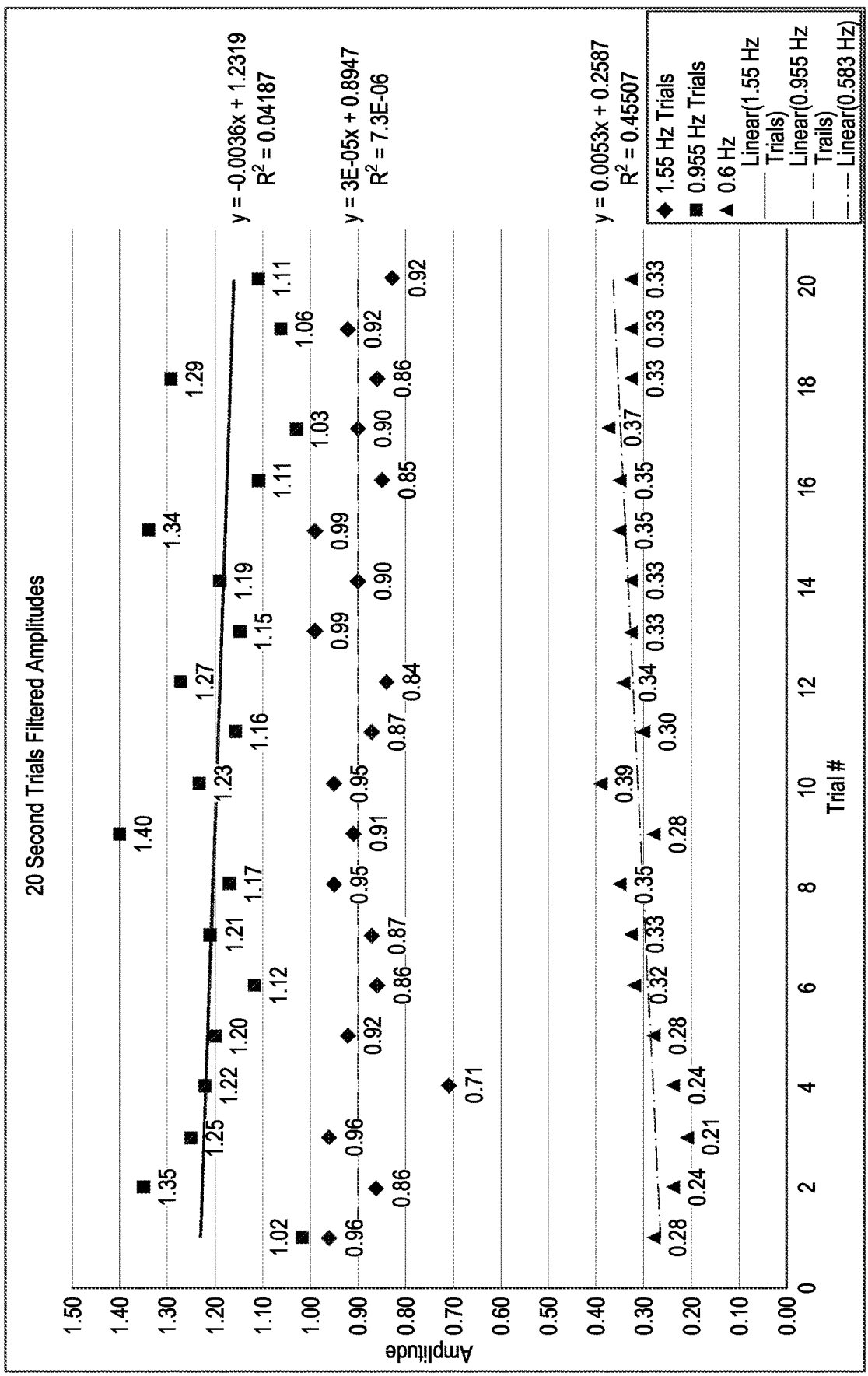
FIG. 9 illustrates sample results of calculated amplitudes of movement from 20 trials of 20 second recordings, with consistent amplitudes using a simulator.
Figure 11:
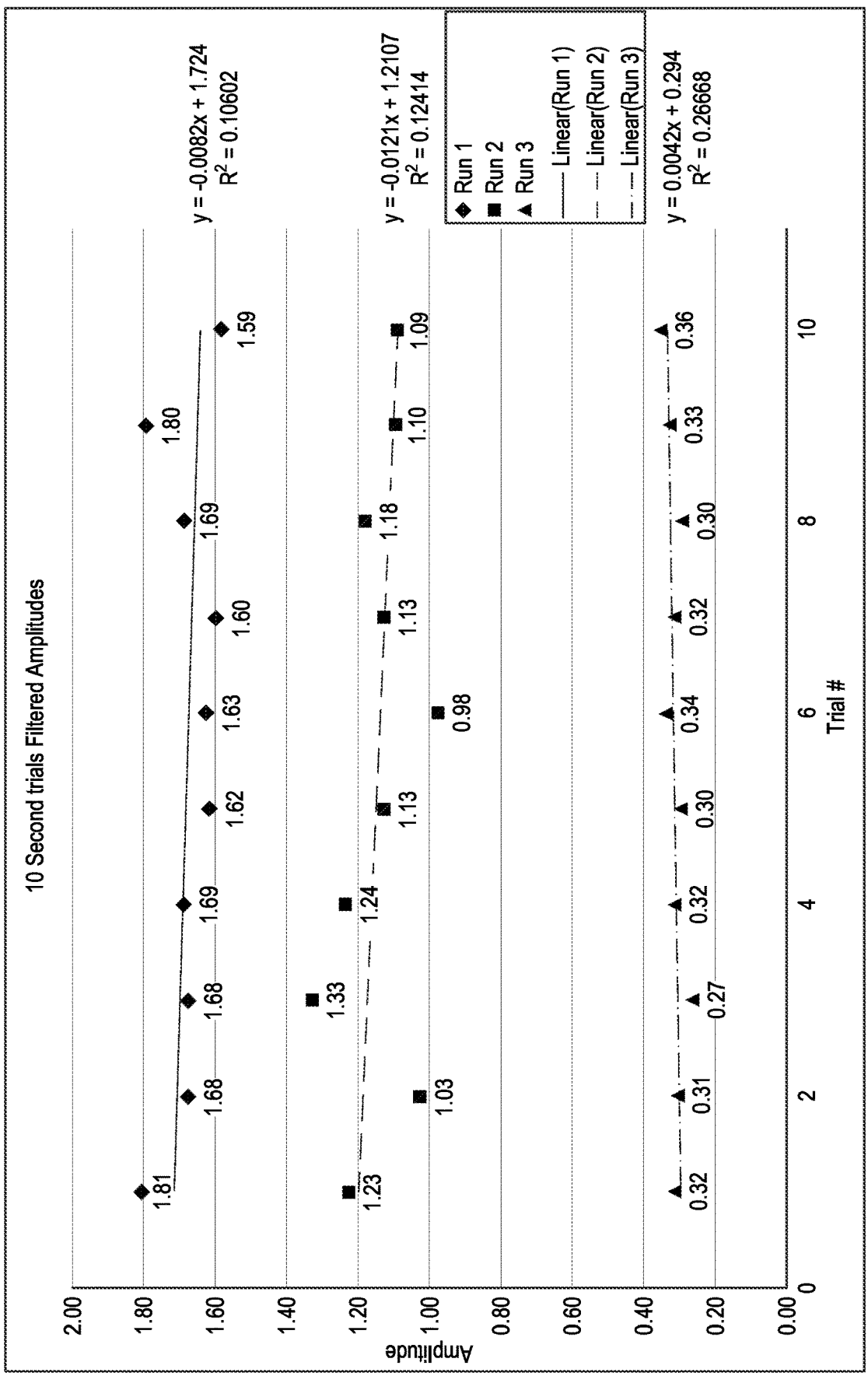
FIG. 11 illustrates sample results of calculated amplitudes from 10 trials of 10 second recordings, with consistent amplitudes using a simulator.

FIG. 9 illustrates sample results again using a "Leap Motion Controller" as the hand tracking system 101 and a simulator with an embodiment similar to that of FIG. 5. These sample results may include 20 different recordings lasting 20 seconds each at three different amplitudes, where the amplitude at a dominant frequency was pre-determined using a control board 125 and verified using high-resolution video as the alternate tracking system 141. The calculated amplitudes at the dominant frequency from the "Leap Motion Controller" were compared to the known predetermined amplitudes and plotted to determine repeatability and accuracy of measuring the amplitude of displacement at the dominant frequency. Similarly, FIG. 11 illustrates different sample results using the same method mentioned, but instead may include ten different recordings lasting ten seconds each for three different known amplitudes. Using these different lengths of recordings may assist in determining whether utilizing less data, from a shorter test, still provides accurate results for determining the dominant amplitude.

The before mentioned methods of comparison 161 are only some particular examples of methods used to verify and validate the accuracy and reproducibility of the hand tracking system 101 against an alternate tracking system 141.

Figure 15:
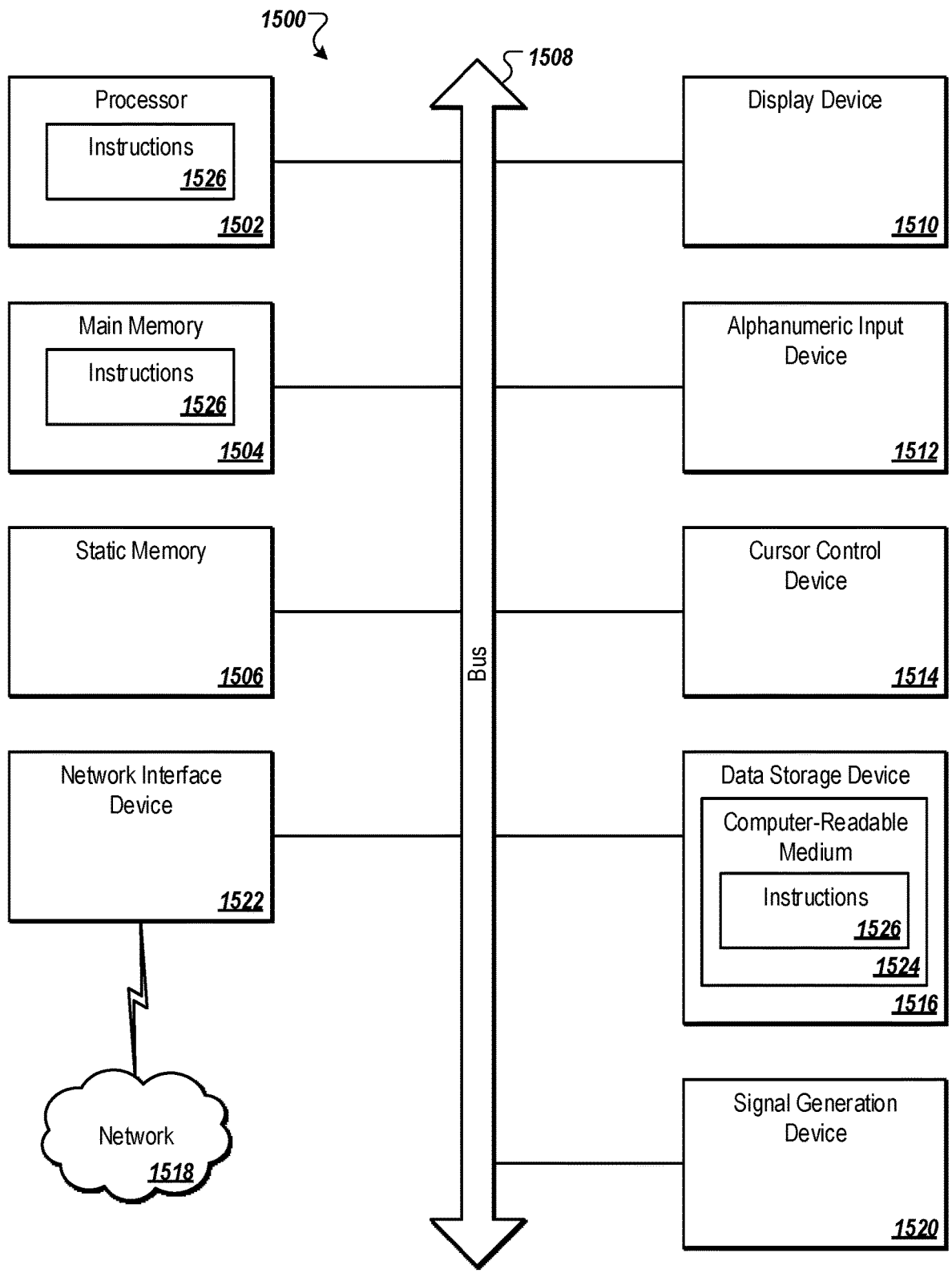
FIG. 15 illustrates a diagrammatic representation of a machine in the example form of a computing device within which a set of instructions, for causing the machine to perform any one or more of the methodologies discussed herein, may be executed, all arranged in accordance with at least one embodiment described herein.

FIG. 15 illustrates a diagrammatic representation of a machine in the example form of a computing device 1500 within which a set of instructions, for causing the machine to perform any one or more of the methodologies discussed herein, may be executed. The computing device 1500 may include a mobile phone, a smart phone, a netbook computer, a rackmount server, a router computer, a server computer, a personal computer, a mainframe computer, a laptop computer, a tablet computer, a desktop computer etc., within which a set of instructions, for causing the machine to perform any one or more of the methods discussed herein, may be executed. In alternative embodiments, the machine may be connected (e.g., networked) to other machines in a LAN, an intranet, an extranet, or the Internet. The machine may operate in the capacity of a server machine in client-server network environment. The machine may be a personal computer (PC), a set-top box (STB), a server, a network router, switch or bridge, or any machine capable of executing a set of instructions (sequential or otherwise) that specify actions to be taken by that machine. Further, while only a single machine is illustrated, the term "machine" may also include any collection of machines that individually or jointly execute a set (or multiple sets) of instructions to perform any one or more of the methods discussed herein.

The example computing device 1500 includes a processing device (e.g., a processor) 1502, a main memory 1504 (e.g., read-only memory (ROM), flash memory, dynamic random access memory (DRAM) such as synchronous DRAM (SDRAM)), a static memory 1506 (e.g., flash memory, static random access memory (SRAM)) and a data storage device 1516, which communicate with each other via a bus 1508.

Processing device 1502 represents one or more general-purpose processing devices such as a microprocessor, central processing unit, or the like. More particularly, the processing device 1502 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1502 may also be one or more special-purpose processing devices such as an application specific integrated circuit (ASIC), a field programmable gate array (FPGA), a digital signal processor (DSP), network processor, or the like. The processing device 1502 is configured to execute instructions 1526 for performing the operations and steps discussed herein.

The computing device 1500 may further include a network interface device 1522 which may communicate with a network 1518. The computing device 1500 also may include a display device 1510 (e.g., a liquid crystal display (LCD) or a cathode ray tube (CRT)), an alphanumeric input device 1512 (e.g., a keyboard), a cursor control device 1514 (e.g., a mouse) and a signal generation device 1520 (e.g., a speaker). In one implementation, the display device 1510, the alphanumeric input device 1512, and the cursor control device 1514 may be combined into a single component or device (e.g., an LCD touch screen).

The data storage device 1516 may include a computer-readable storage medium 1524 on which is stored one or more sets of instructions 1526 embodying any one or more of the methodologies or functions described herein. The instructions 1526 may also reside, completely or at least partially, within the main memory 1504 and/or within the processing device 1502 during execution thereof by the computing device 1500, the main memory 1504 and the processing device 1502 also constituting computer-readable media. The instructions may further be transmitted or received over a network 1518 via the network interface device 1522.

While the computer-readable storage medium 1524 is shown in an example embodiment to be a single medium, the term "computer-readable storage medium" may include a single medium or multiple media (e.g., a centralized or distributed database and/or associated caches and servers) that store the one or more sets of instructions. The term "computer-readable storage medium" may also include any medium that is capable of storing, encoding or carrying a set of instructions for execution by the machine and that cause the machine to perform any one or more of the methodologies of the present disclosure. The term "computer-readable storage medium" may accordingly be taken to include, but not be limited to, solid-state memories, optical media and magnetic media.

In one aspect, a system includes a memory. The system further includes a communications interface. The system further includes at least one sensor to measure a signal associated with position or motion of an extremity of a subject. The system further includes a processor operatively coupled to the memory, the communications interface, and the sensor. The processor is configured to perform operations includes receive the signal from the sensor. The processor is configured to communicate, via the communications interface, the signal, login credentials, and position or motion data to a remote server coupled to a remote server. The remote server is configured to receive the signal and perform an analysis that quantifies a severity of tremor based on the position or motion signals of the subject. The processor is configured to receive the analysis that quantified the severity of tremor. The processor is configured to cause the quantified severity of tremor to be displayed via a display device.

Implementations can include any, all, or none of the following features. One of the sensors can be not in physical contact with the subject to record the position or motion of the subject. Said measurement of the subject's tremor can be applied to early therapeutic intervention in Parkinson's Disease. The processor can be further configured to at least partially identify a clinical drug candidate in pharmaceutical development by confirming therapeutic target engagement in-vivo, b) screen for and diagnose early disease such as prodromal Parkinson's Disease, and c) enable in-office as well as home and portable monitoring of therapeutic interventions. The remote server can be coupled to an electronic health records database. The electronic health records database can be configured to store and maintain the subject's resulting analysis and signal from the remote server for an individual user associated with login credentials for identity verification. The remote server can be configured to send the resulting analysis to the electronic health records database. The electronic health records database can include a records server that can be configured to generate a database, in response to the receipt of subject results and analysis from the remote server. The records server can include a processor to perform operations that can include maintain in memory the signals received from the remote server that can include the analysis of and signals used to quantify tremor severity. The processor can further perform operations that include generate a database that can include subject data that can be associated and stored, according to the login credentials. The processor can further perform operations that include output, as a result of a query, the analysis and signals from the database in electronic form to a remote platform for viewing provided that correct login credentials can be provided. The sensor can be qualified for accuracy using a simulator that can include a phantom capable to produce a reproducible movement and comparing the results of the external sensor with an alternate method of measuring position and motion. The qualification can be for early therapeutic intervention in Parkinson's Disease.

In one aspect, a system includes a memory. The system further includes a communications interface. The system further includes a processor operatively coupled to the memory, the communications interface, and a peripheral sensor. The peripheral sensor is configured to measure a signal associated with position or motion of an extremity of a subject. The processor is configured to perform operations includes receive a signal from the peripheral sensor. The processor is configured to communicate, via the communications interface, the signal, login credentials, and position or motion data to a remote server coupled to a remote server. The remote server is configured to receive the signal and perform an analysis that quantifies a severity of tremor based on the position or motion signals of the subject. The processor is configured to receive the analysis that quantified the severity of tremor. The processor is configured to cause the quantified severity of tremor to be displayed via a display device.

Implementations can include any, all, or none of the following features. The sensor can be not in physical contact with the subject to record the position or motion of the subject. Said measurement of a subject's tremor can be applied to early therapeutic intervention in Parkinson's Disease. The processor can be further configured to at least partially identify a clinical drug candidate in pharmaceutical development by confirming therapeutic target engagement in-vivo. The processor can be further configured to at least partially screen for and diagnose early disease such as prodromal Parkinson's Disease. The processor can be further configured to enable in-office and home and portable monitoring of therapeutic interventions. The remote server can be coupled to an electronic health records database. The electronic health records database can be configured to store and maintain the subject's resulting analysis and signal from the remote server for an individual user associated with the login credentials for identity verification. The remote server can be configured to send the resulting analysis to the electronic health records database. The electronic health records database can include a records server that can be configured to generate a database, in response to the receipt of subject results and analysis from the remote server. The records server can include a processor to perform operations can include maintain in memory the signals received from the remote server that can include the analysis of and signals used to quantify tremor severity. The processor is configured to generate a database that can include individual data that can be associated and stored, according to the login credentials. The processor is configured to output, as a result of a query, the analysis and signals from the database in electronic form to a remote platform for viewing provided that correct login credentials can be provided. The sensor can be qualified for accuracy using a simulator that can include a phantom capable to produce a reproducible movement and comparing the results of the external sensor with an alternate method of measuring position and motion. The qualification can be for early therapeutic intervention in Parkinson's Disease.

In one aspect, a method includes receiving, from at least one sensor, a signal indicative of a change in position or motion of an extremity of a subject. The method further includes communicating, via a communications interface, the signal, login credentials, and position or motion data to a remote server coupled to a remote electronic health record database. The remote server is configured to receive the signal and perform an analysis that quantifies a severity of tremor based on the position or motion signals of the subject. The method further includes receiving the analysis that quantified the severity of tremor. The method further includes causing the quantified severity of tremor to be displayed via a display device.

Implementations can include any, all, or none of the following features. One of the sensors can be not in physical contact with the subject to record the position or motion of the subject.

Terms used herein and especially in the appended claims (e.g., bodies of the appended claims) are generally intended as "open" terms (e.g., the term "including" may be interpreted as "including, but not limited to," the term "having" may be interpreted as "having at least," the term "includes" may be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases may not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" may be interpreted to mean "at least one" or "one or more"); the same holds true for the use of definite articles used to introduce claim recitations.

In addition, even if a specific number of an introduced claim recitation is explicitly recited, those skilled in the art will recognize that such recitation may be interpreted to mean at least the recited number (e.g., the bare recitation of "two recitations," without other modifiers, means at least two recitations, or two or more recitations). Further, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, may be understood to contemplate the possibilities of including one of the terms, either of the terms, or both terms. For example, the phrase "A or B" may be understood to include the possibilities of "A" or "B" or "A and B."

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions may include, for example, instructions and data which cause a general purpose computer, special purpose computer, or special purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general purpose hardware), specific hardware implementations or a combination of software and specific hardware implementations are also possible and contemplated. In this description, a "computing entity" may be any computing system as previously defined herein, or any module or combination of modulates running on a computing system.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it may be understood that the various changes, substitutions, and alterations may be made hereto without departing from the spirit and scope of the present disclosure.

What is claimed is:

1. A system, comprising:
    a memory;
    a communications interface;
    at least one sensor to measure a signal associated with position or motion of an extremity of a subject, wherein the at least one sensor includes a portable optical sensor and wherein the portable optical sensor is qualified for accuracy by:
        using a tremor simulator device that includes a hand phantom capable to produce a simulated movement of a human hand;
        measuring movement of the hand phantom using the at least one sensor and an alternate method of measuring position and motion;
        comparing the results of the at least one sensor with the alternate method of measuring position and motion; and
        determining to qualify the at least one sensor based on the comparison of the results and based on at least one statistical analysis metric indicative of reproducible accuracy, wherein the at least one sensor is qualified based on the at least one statistical analysis metric meeting a predetermined threshold; and
    a processor operatively coupled to the memory, the communications interface, and the sensor, wherein the processor is configured to perform operations comprising:
        receive the signal from the sensor;
        communicate, via the communications interface, the signal, login credentials, and position or motion data to a remote server, wherein the remote server is configured to receive the signal and perform an analysis that quantifies a severity of tremor based on the position or motion signals of the subject; and
        receive the analysis that quantified the severity of tremor.

2. The system of claim 1, wherein the quantified severity of tremor is compared to at least one reference value, and based on the comparison, further color coded when displayed via a display device.

3. The system of claim 1, wherein the optical sensor includes a depth camera or 3D camera.

4. The system of claim 1, wherein the processor is further configured to perform monitoring of system is further applied to early therapeutic intervention by the quantified severity of tremor.

5. The system of claim 4, wherein the early therapeutic intervention includes a non-drug early intervention approach.

6. The system of claim 5, wherein the non-drug early intervention approach includes brain stimulation.

7. The system of claim 6, wherein the brain stimulation includes one or more of: deep brain stimulation (DBS), Transcranial magnetic stimulation (TMS), transcranial direct current stimulation (tDCS), transcutaneous electrical nerve stimulation (TENS).

8. The system of claim 5, wherein the non-drug early intervention approach is focused ultrasound.

9. A method, comprising:
    receiving, from at least one sensor, a signal indicative of a change in position or motion of an extremity of a subject, wherein one sensor of the at least one sensor includes an optical sensor or a wearable sensor, wherein the at least one sensor is qualified for accuracy by:
  using an artificial hand tremor simulator that includes a human hand phantom capable to produce a reproducible movement;
  comparing the results of the at least one sensor with an alternate method of measuring position and motion; and
  determining to qualify the at least one sensor based on the comparison of the results; and
communicating, via a communications interface, the signal to a processor coupled to a remote electronic health record database, wherein the processor is configured to receive the signal and perform an analysis that quantifies a severity of tremor based on the position or motion signals of the subject.

10. The method of claim 9, wherein the quantified severity of tremor is compared to at least one reference value, and based on the comparison, further color coded when displayed via a display device.

11. The method of claim 9, wherein the optical sensor includes a depth camera or 3D camera.

12. The method of claim 9, wherein the method is applied to early therapeutic intervention.

13. The method of claim 12, wherein the early therapeutic intervention includes a non-drug early intervention approach.

14. The method of claim 13, wherein the non-drug early intervention approach includes brain stimulation.

15. The method of claim 14, wherein the brain stimulation includes one or more of: deep brain stimulation (DBS), Transcranial magnetic stimulation (TMS), transcranial direct current stimulation (tDCS), transcutaneous electrical nerve stimulation (TENS).

16. The method of claim 13, wherein the non-drug early intervention approach is focused ultrasound.

17. The method of claim 9, wherein the quantified tremor severity is further combined with an olfactory test and/or genetic data to direct patients to positron emission tomography (PET) imaging.

18. The method of claim 9, further comprising:
  at least partially identifying a clinical drug candidate in pharmaceutical development by confirming therapeutic target engagement in-vivo;
  at least partially screening for and diagnosing early disease such as prodromal Parkinson's Disease; or
  enabling in-office and home and portable monitoring of therapeutic interventions.

* * * * *

UNITED STATES PATENT AND TRADEMARK OFFICE
CERTIFICATE OF CORRECTION

PATENT NO. : 11,723,582 B2
APPLICATION NO. : 17/364664
DATED : August 15, 2023
INVENTOR(S) : Matthew J. Johnson et al.

Page 1 of 1

It is certified that error appears in the above-identified patent and that said Letters Patent is hereby corrected as shown below:

In the Claims

Column 18, Line 49 (Claim 4): delete "system is further applied to".

Column 18, Line 50 (Claim 4): add a "," after 'intervention'.

Signed and Sealed this
Twenty-first Day of November, 2023

Katherine Kelly Vidal
*Director of the United States Patent and Trademark Office*